United States Patent
Buschle

(10) Patent No.: US 10,921,005 B2
(45) Date of Patent: Feb. 16, 2021

(54) METHOD OF OPERATING A HUMIDIFYING MODULE, HUMIDIFYING MODULE, AND INCUBATOR OR CLIMATIC CHAMBER WITH HUMIDIFYING MODULE

(71) Applicant: Binder GmbH, Tuttlingen (DE)

(72) Inventor: Jochen Buschle, Tuttlingen (DE)

(73) Assignee: Binder GmbH, Tuttlingen (DE)

( * ) Notice: Subject to any disclaimer, the term of this patent is extended or adjusted under 35 U.S.C. 154(b) by 236 days.

(21) Appl. No.: 15/926,033

(22) Filed: Mar. 20, 2018

(65) Prior Publication Data
US 2018/0266713 A1 Sep. 20, 2018

(30) Foreign Application Priority Data
Mar. 20, 2017 (DE) ...................... 10 2017 105 8923

(51) Int. Cl.
*F24F 6/02* (2006.01)
*C12M 1/34* (2006.01)
(Continued)

(52) U.S. Cl.
CPC ............. *F24F 6/025* (2013.01); *C12M 29/26* (2013.01); *C12M 41/00* (2013.01); *C12M 41/12* (2013.01);
(Continued)

(58) Field of Classification Search
CPC ...... C12M 29/26; C12M 41/00; C12M 41/12; C12M 41/14; C12M 41/22; C12M 41/34;
(Continued)

(56) References Cited

U.S. PATENT DOCUMENTS 4,923,816 A * 5/1990 Heeg .................. B01L 7/02
219/401
2013/0263851 A1* 10/2013 Arcilla .............. A61M 16/1075
128/203.14
(Continued)

FOREIGN PATENT DOCUMENTS

DE 102014110965 2/2016
EP 0340341 11/1989
(Continued)

OTHER PUBLICATIONS

European Patent Office, "Search Report," issued in European Patent Application No. 18159932.5, document of 8 pages, dated Aug. 17, 2018.

*Primary Examiner* — Robert Clemente
(74) *Attorney, Agent, or Firm* — Akerman LLP; Peter A. Chiabotti

(57) ABSTRACT

A method of operating a humidifying module for an incubator, the humidifying module having a container with a water inlet and a steam outlet, a heating device which is arranged in the interior of the container, and a temperature sensor and a control circuit for controlling or regulating a water supply through the water inlet and/or for controlling or regulating a heat output of the heating device, wherein container is filled with water, at a maximum, so that a steam volume remains, in which there is steam generated when heating with the heating device, wherein part of the heating device protrudes from the water and projects into the steam volume, so that the steam can be superheated, and wherein the temperature sensor is arranged to directly or indirectly measure the temperature of the steam, the measured temperature being used as a control parameter by the control (Continued)

circuit, a humidifying module for an incubator for carrying out such a method, and an incubator with such a humidifying module.

11 Claims, 3 Drawing Sheets

(51) Int. Cl.
| | |
|---|---|
| *C12M 1/02* | (2006.01) |
| *F24F 6/18* | (2006.01) |
| *C12M 1/00* | (2006.01) |
| *C12M 1/36* | (2006.01) |
| *F24F 11/00* | (2018.01) |
| *F24F 6/00* | (2006.01) |

(52) U.S. Cl.
CPC ............ *C12M 41/14* (2013.01); *C12M 41/22* (2013.01); *C12M 41/34* (2013.01); *C12M 41/48* (2013.01); *F24F 6/18* (2013.01); *F24F 11/0008* (2013.01); *F24F 2006/008* (2013.01)

(58) Field of Classification Search
CPC .. C12M 41/48; F24F 6/025; F24F 6/18; F24F 11/0008; F24F 2006/008; A61M 16/162
See application file for complete search history.

(56) References Cited

U.S. PATENT DOCUMENTS

| | | |
|---|---|---|
| 2014/0238496 A1 | 8/2014 | Öffner |
| 2017/0073628 A1 | 3/2017 | Zander et al. |

FOREIGN PATENT DOCUMENTS

| | | |
|---|---|---|
| EP | 2770047 | 8/2014 |
| WO | 2012/093326 | 7/2012 |
| WO | 2015172882 | 11/2015 |

* cited by examiner

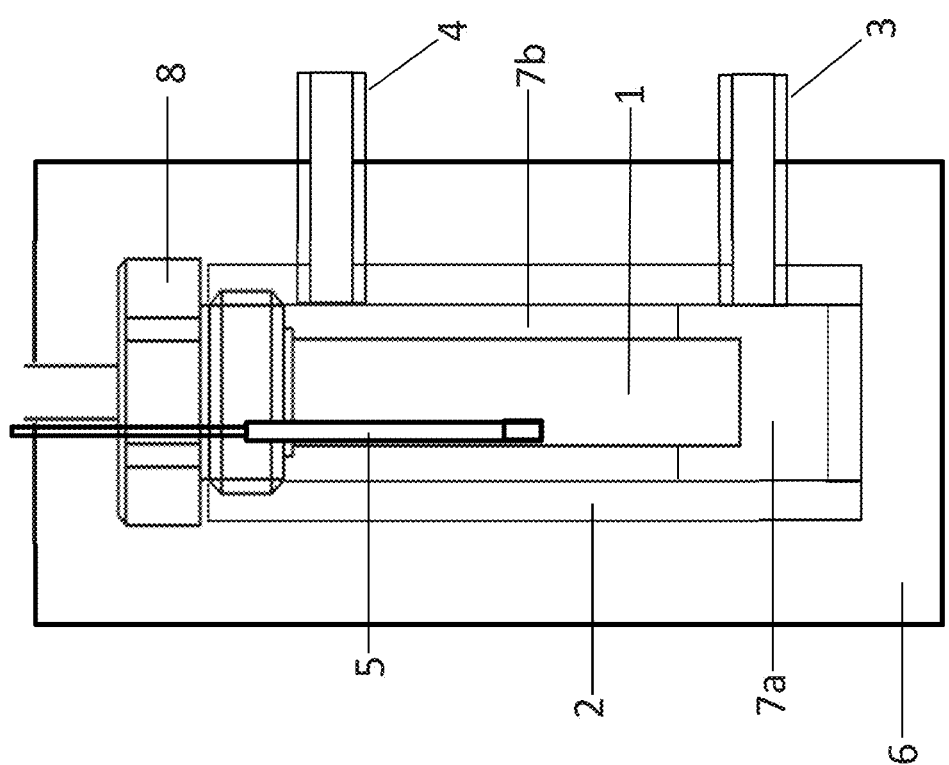

METHOD OF OPERATING A HUMIDIFYING MODULE, HUMIDIFYING MODULE, AND INCUBATOR OR CLIMATIC CHAMBER WITH HUMIDIFYING MODULE

CROSS-REFERENCE TO RELATED APPLICATIONS

This application claims priority to German Patent Application No. 10 2017 105 892.3, filed Mar. 20, 2017, which is incorporated by reference in its entirety.

SUMMARY

Using incubators or climatic chambers, it is possible to produce defined climatic conditions in a test space located inside the incubator or climatic chamber, in particular a predetermined temperature and humidity. Humidity is an important parameter in many applications, such as incubation of cells, where sometimes humidity>90% rel. hum. must be set and maintained. However, in many cases, it has hitherto been regulated simply by placing a water reservoir, e.g. a bowl of water, in the incubator or climatic chamber, which then passes into the air in the interior of the incubator or climatic chamber through evaporation at the temperatures prevailing in the incubator or climatic chamber.

Opening the door especially interferes with the climate in the incubator or climatic chamber, as a result of which in particular the humidity falls below the required value. In order to keep the impacts of such deviations from the target values as low as possible, a short humidity recovery time is preferable, which in particular requires ensuring as continuous a humidifying as possible.

The present disclosure provides a method of operating a humidifying module, the humidifying module being suitable, in particular, for an incubator or climatic chamber, a humidifying module for carrying out the method, which is suitable, in particular, for an incubator or climatic chamber, and an incubator or climatic chamber with such a humidifying module, by means of which a continuous humidifying can be ensured in a simple and efficient way.

The present disclosure provides a method of operating a humidifying module having the features and structures recited herein. Advantageous embodiments of the present disclosure are further recited herein.

The method according to the present disclosure is used to operate a humidifying module, which is suitable in particular for an incubator or climatic chamber, the humidifying module having a container with a water inlet and a steam outlet, a heating device which is arranged in the interior of the container, and a temperature sensor and a control circuit for controlling or regulating a water supply through the water inlet and/or for controlling or regulating a heat output of the heating device.

The present disclosure provides that the container is filled with water, at a maximum, so that a steam volume remains in which there is steam generated when heating with the heating device, e.g. an electric heating cartridge, that part of the heating device protrudes from the water and projects into the steam volume—which is also the case when a part of the heater passes through the steam volume—so that the steam can be superheated, and that the temperature sensor is arranged to directly or indirectly measure the temperature of the steam, the measured temperature being used as a control parameter by the control circuit. A direct measurement is a measurement where the measuring point of the temperature sensor is within the steam volume; however, indirect measurements are also possible in which the measuring point of the temperature sensor is arranged on the container wall in the area of the steam volume or is arranged in the interior of the heating device.

To generate steam, the water is heated by heating with the heating device, so that steam passes into the steam volume. There, the steam is heated further, as a result of which it is superheated and thereby rises further in the direction of the steam outlet, through which it can pass into the interior of the incubator or climatic chamber for humidifying, if desired. In addition to the fact that this mode of operation allows to operate an unpressurized system, which allows a simple and cost-effective design and also facilitates the registration, by superheating the steam in the steam volume sterilization is achieved also, so that the risk of foreign organisms entering the incubator or climatic chamber is significantly reduced.

According to the present disclosure the direct or indirect temperature monitoring of the steam temperature is also used as a control parameter. On the one hand, in this way, the refilling of water can be controlled by the control circuit filling water into the container via the water inlet, upon reaching or exceeding a threshold of the temperature of the steam measured by the temperature sensor. In continuous operation of the humidifying module, the water level declines as more and more water is evaporated. Accordingly, the resulting steam is superheated more and more because the steam volume increases with declining water level and thus an ever larger part of the heating device protrudes from the water. At a given heat output, it is thus possible to draw conclusions about the current water level from the steam temperature that is reached, allowing a timely automatic refilling and thus operation as continuously as possible.

However, it is also possible to reduce the load of the humidifying module when the humidifying module is operated in a standby mode when it does not have to dispense humidity in the form of steam. In this standby mode, the heat output of the heating element in the standby mode is then regulated by the control circuit using the temperature measured by the temperature sensor so that the temperature remains below the boiling temperature.

The humidifying module according to the present disclosure, which is particularly suitable for carrying out such a method for an incubator or climatic chamber, has a container with a water inlet and a steam outlet, a heating device which is arranged in the interior of the container such that it protrudes partially from the water even at maximum filling of the container with water, a temperature sensor and a control circuit configured to control or regulate a water supply through the water inlet and/or to control or regulate a heat output of the heating device based on measurements of the temperature sensor.

It should be noted that a maximum filling of the container is already predetermined by the position of the steam outlet, which must necessarily be above the water level, so that the water does not run out. Implicitly, the container interior is thus always divided into a steam volume and a liquid volume, with the liquid volume at the bottom and the steam volume at the top. As evaporation increases, the boundary between these two volumes shifts.

This is especially true with lateral arrangement of the steam outlet. Even in cases where there is no mark to specify a maximum water level, a maximum filling of the container is predetermined by the structure of the container.

In a first embodiment, the temperature sensor is arranged on the outer jacket of the container above the maximum water level at the level of the steam volume. Alternatively, the temperature sensor may be arranged within the steam volume or within the heating device.

It is particularly preferred if the control circuit is configured to fill water into the container via the water inlet when the threshold of the temperature of the steam measured by the temperature sensor is reached or exceeded.

Alternatively or additionally, the control circuit may be preferably configured to operate the humidifying module in a standby mode when it does not have to dispense humidity in the form of steam, and is further configured to regulate the heat output of the heating element in standby mode by the control circuit using the temperature measured by the temperature sensor so that the temperature remains below the boiling temperature.

The incubator or climatic chamber according to the present application is characterized in that it has a humidifying module according to the present disclosure.

BRIEF DESCRIPTION OF THE DRAWINGS

The subject matter of the present application will be explained in more detail with reference to figures showing exemplary embodiments in which:

FIG. 3 shows a third humidifying module, in particular for an incubator or climatic chamber.

FIG. 1 shows a humidifying module 10 which is suitable, in particular, for an incubator or climatic chamber. The humidifying module 10 has a container 2, the interior of which is divided into a liquid volume 7a filled with water, which for physical reasons is at the bottom, and a steam volume 7b above. In the area of liquid volume 7a, a lateral water inlet 3 is provided, while in the area of the steam volume 7b there is a steam outlet 4, which at the same time defines a maximum water level, so that a steam volume 7b always remains in container 2. Container 2 is thermally insulated with an insulating layer 6 to allow more energy efficient operation of humidifying module 10.

Figure 1:
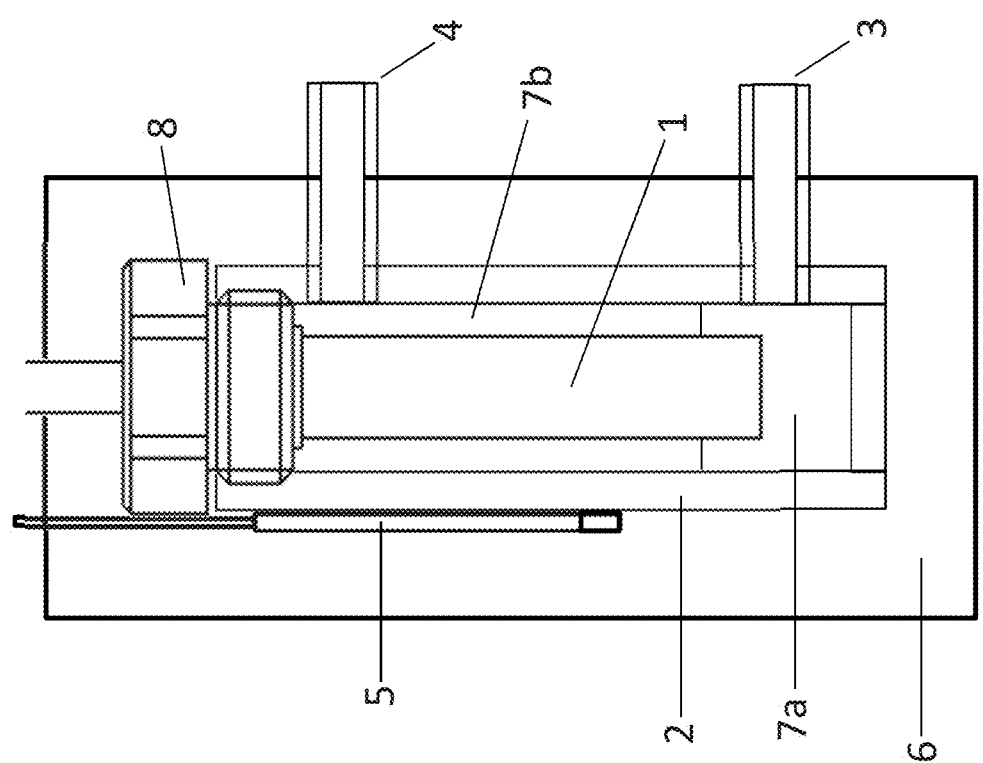
FIG. 1 shows a first humidifying module, in particular for an incubator or climatic chamber.

Also arranged in container 2 is a heating device 1, which may for example be designed as a self-limiting PTC heating cartridge. The heating device 1 is not completely covered by water, but protrudes from the water and projects into steam volume 7b. In the exemplary embodiment shown, the heating device 1 is arranged on a cover 8 of the container and thus extends through the entire steam volume 7b.

Accordingly, during operation of humidifying module 10, water is heated with heating device 1 and rises as steam to steam volume 7b. Because heat output is still provided in this steam volume 7b by heating device 1, there is superheating of the steam, which then can, if necessary, pass through the steam outlet 4 present in the upper area of the container into the the interior of the incubator (not shown) and provide there the desired humidification.

In the area of steam volume 7b, a temperature sensor 5, for example a PT-100 element, is arranged adjoining an outer wall of the container, with which the temperature of the superheated steam is indirectly detected here. The measurements of temperature sensor 5 are forwarded to a control circuit (not shown in FIG. 1) which, in particular when the measured temperature exceeds a threshold, causes the refilling of water through water inlet 3.

If humidity does not have to be supplied to the incubator or climatic chamber, humidifying module 10 is operated by the control circuit in a standby mode in which the heat output of heating device 1 is reduced so that the temperature measured at temperature sensor 5 is below the boiling temperature and is stabilized just below the boiling point by using the data of temperature sensor 5 as parameter, so that when there is again a need for humidity in the interior of the incubator or climatic chamber steam can be provided again quickly by increasing the heat output of heater 1, at the same time, however, as long as that is not the case, humidifying module 10 is operated in a less heavily loaded mode of operation.

Figure 2:
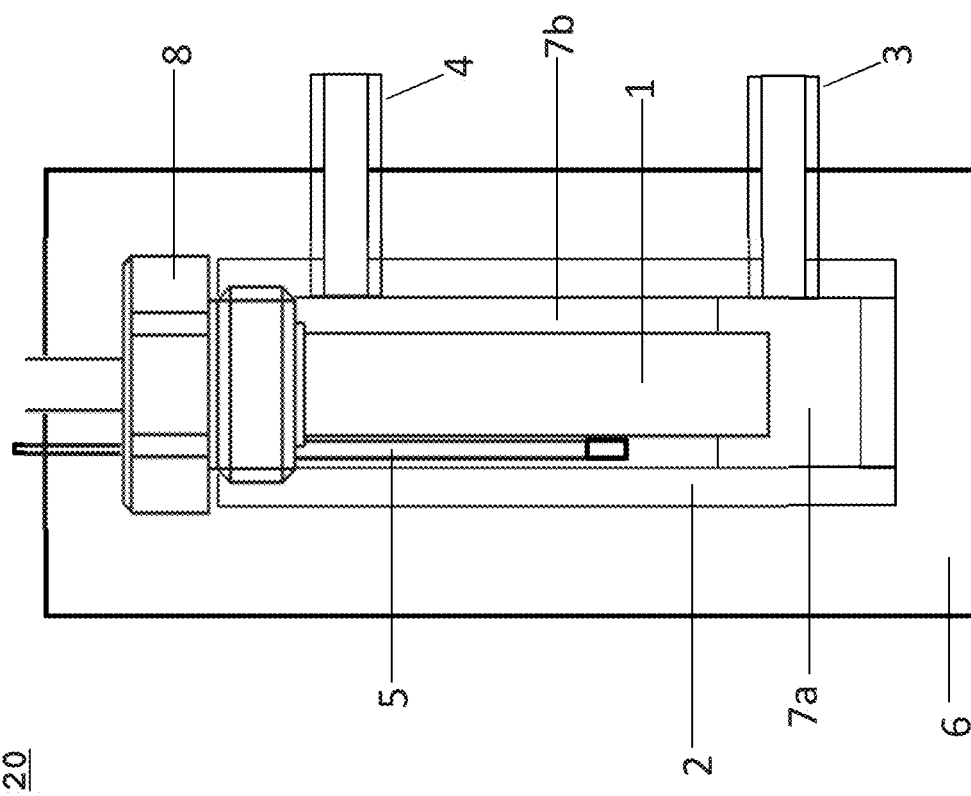
FIG. 2 shows a second humidifying module, in particular for an incubator or climatic chamber.

Humidifying modules 20 and 30, which are shown in FIGS. 2 and 3, have the same components, which are therefore also identified by the same reference numerals. The difference between the humidifying modules 10,20,30 is merely in the arrangement of temperature sensor 5. In FIG. 2, it is arranged directly in steam volume 7b, which brings about a direct measurement. In FIG. 3, it is included in the interior of heating device 1.

| List of reference numerals | |
| --- | --- |
| 1. | heating device |
| 2. | container |
| 3. | water inlet |
| 4. | steam outlet |
| 5. | temperature sensor |
| 6. | insulation layer |
| 7a | liquid volume |
| 7b | steam volume |
| 8 | cover |
| 10, 20, 30 | humidifying volume |

The invention claimed is:

1. A method of operating a humidifying module, comprising:
   providing a closed container with an interior subdivided into a steam volume and a liquid volume, wherein the steam volume is arranged above a water level of the liquid volume determined by a water fill level, a water inlet, a steam outlet, a heating device arranged in the interior of the container, a temperature sensor and a control circuit that controls a water supply through the water inlet and controls a heat output of the heating device;
   filling the container with water, at a maximum, so that a steam volume remains in the container and in which there is steam generated when heating with the heating device, wherein the steam outlet specifies the maximum water level, and wherein part of the heating device protrudes from the water and projects into the steam volume;
   superheating the steam in the steam volume;
   measuring the temperature of the steam in the steam volume in the container, where the temperature sensor is positioned on an outer wall of the container in the area of the steam volume, within the steam volume or within the heating device to directly or indirectly measure the temperature of the steam, and
   controlling the water supply and the heat output of the heating device with the control circuit based on a measured temperature of the steam.

2. The method according to claim 1, further comprising filling the container with water via the water inlet, wherein the filling the container is regulated by the control circuit when a threshold of the temperature of the steam measured by the temperature sensor is reached.

3. The method according to claim 1, further comprising:
operating the humidifying module in a standby mode when steam is not dispensed; and
controlling, via the control circuit, a heat output of the heating device in the standby mode using the temperature of the steam measured by the temperature sensor so that the temperature of the steam remains below boiling temperature of water.

4. The method according to claim 1, further comprising:
collecting steam in the steam volume of the closed container; and
purging superheated steam through the steam outlet.

5. A humidifying module, comprising:
a closed container comprising:
  an interior subdivided into a steam volume and a liquid volume, wherein the steam volume is arranged above a water level of the liquid volume determined by a water fill level;
  a water inlet;
  a steam outlet specifying a maximum water level;
  a heating device arranged in the interior of the closed container such that the heating device is partially submerged under the water level and the heating device protrudes partially out of the water level even with maximum filling of the container with water;
a temperature sensor positioned on an outer wall of the closed container in the area of the steam volume, within the steam volume or within the heating device; and
a control circuit that controls a water supply through the water inlet and controls a heat output of the heating device.

6. The humidifying module according to claim 5, wherein the temperature sensor is arranged on an outer jacket of the container above a maximum water level at a level of a steam volume.

7. The humidifying module according to claim 5, wherein the temperature sensor is arranged within the steam volume.

8. The humidifying module according to claim 5, wherein the temperature sensor is arranged within the heating device.

9. The humidifying module according to claim 5, wherein the control circuit is configured to fill water into the container via the water inlet when a threshold of a temperature of steam of the steam volume measured by the temperature sensor is reached or exceeded.

10. The humidifying module according to claim 5, wherein the control circuit operates in a standby mode when steam is not dispensed in, and wherein the control circuit is further configured to regulate heat output of the heating device in the standby mode by the control circuit using a temperature measured by the temperature sensor so that the temperature of the steam remains below a boiling temperature.

11. The humidifying module according to claim 5, wherein the heating device is configured to superheat steam in the steam volume and the superheated steam is purged through the steam outlet.

* * * * *